(12) United States Patent
Schindler et al.

(10) Patent No.: US 6,489,453 B1
(45) Date of Patent: Dec. 3, 2002

(54) CHANDRA: A TH1-SPECIFIC GENE

(75) Inventors: Ulrike Schindler, Bad Abbach (DE); Chandrasekar Venkataraman, Daly City, CA (US)

(73) Assignee: Tularik Inc., South San Francisco, CA (US)

( * ) Notice: Subject to any disclaimer, the term of this patent is extended or adjusted under 35 U.S.C. 154(b) by 0 days.

(21) Appl. No.: 09/694,094

(22) Filed: Oct. 20, 2000

Related U.S. Application Data

(60) Provisional application No. 60/161,201, filed on Oct. 22, 1999.

(51) Int. Cl.$^7$ .................. C07H 21/04; C12N 15/12; C12N 15/63
(52) U.S. Cl. .................. 536/2.35; 536/23.1; 435/320.1; 435/252.3; 435/325
(58) Field of Search ............... 536/23.1, 23.5; 435/320.1, 252.3, 325

(56) References Cited

FOREIGN PATENT DOCUMENTS

WO    WO 98/14470    4/1998

OTHER PUBLICATIONS

Attwood Scinece 2000; 290:471–473.*
Skolnick et al. Trends in Biotech. 20000; 18(1):34–39.*
Metzler et al. Nature Structural Biol. 1997; 4:527–531.*
Lerner Nature 1982; 299:592–596, see p. 595–596.*
Bubien et al., *J. Cell Biol*, 121(5):1121–1132 (1993).
Carter et al., *J. Exp. Med.*, 189(8):1355–1360 (1999).
Diatchenko et al., *PNAS*, 93:6025–6030 (1996).
Ferber et al., *Clin. Immunol.*, 91(2):134–144 (1999).
Kaplan et al., *Immunity*, 4:313–319 (1996).
Kaplan et al., *Nature*, 382:174–177 (1996).
Kyte et al., *J. Mol. Biol.*, 157:105–132 (1982).
Marra et al., *Database EMBL*, Accession No. AA161823 (1996).
Marra et al., *Database EMBL*, Accession No. AA762251 (1998).
Mikita et al., *Mol Cell Biol.*, 16(10):5811–582 (1996).
Thierfelder et al., *Nature*, 382:171–174 (1996).
Venkataraman et al., *Cytokine*, 11(11):969 (1999).
Venkataraman et al., *J. of Immunology*, 165(2):632–636 (2000).
Zhang et al., *J. Biol. Chem.*, 272(34):21597–21603 (1997).
Zheng et al., *Cell*, 89:587–596 (1997).

* cited by examiner

*Primary Examiner*—Phillip Gambel
*Assistant Examiner*—Jessica H. Roark
(74) *Attorney, Agent, or Firm*—Townsend & Townsend & Crew LLP

(57) ABSTRACT

The present invention provides nucleic acid and protein sequences for a Th-1 cell-specific protein, Chandra. The herein-disclosed sequences can be used for any of a number of purposes, including for the specific detection of Th1 lymphocytes, for the identification of molecules that associate with and/or modulate the activity of Chandra, to diagnose any of a number of conditions associated with Th1 or Th2 cell activity, or to modulate the number and/or activity of Th1 or Th2 lymphocytes in a mammal.

16 Claims, 2 Drawing Sheets

MQGQEQTTMA VVPGVAVPSK NSVMTSQMWN EKKEKFLKGE  40

Figure 2:
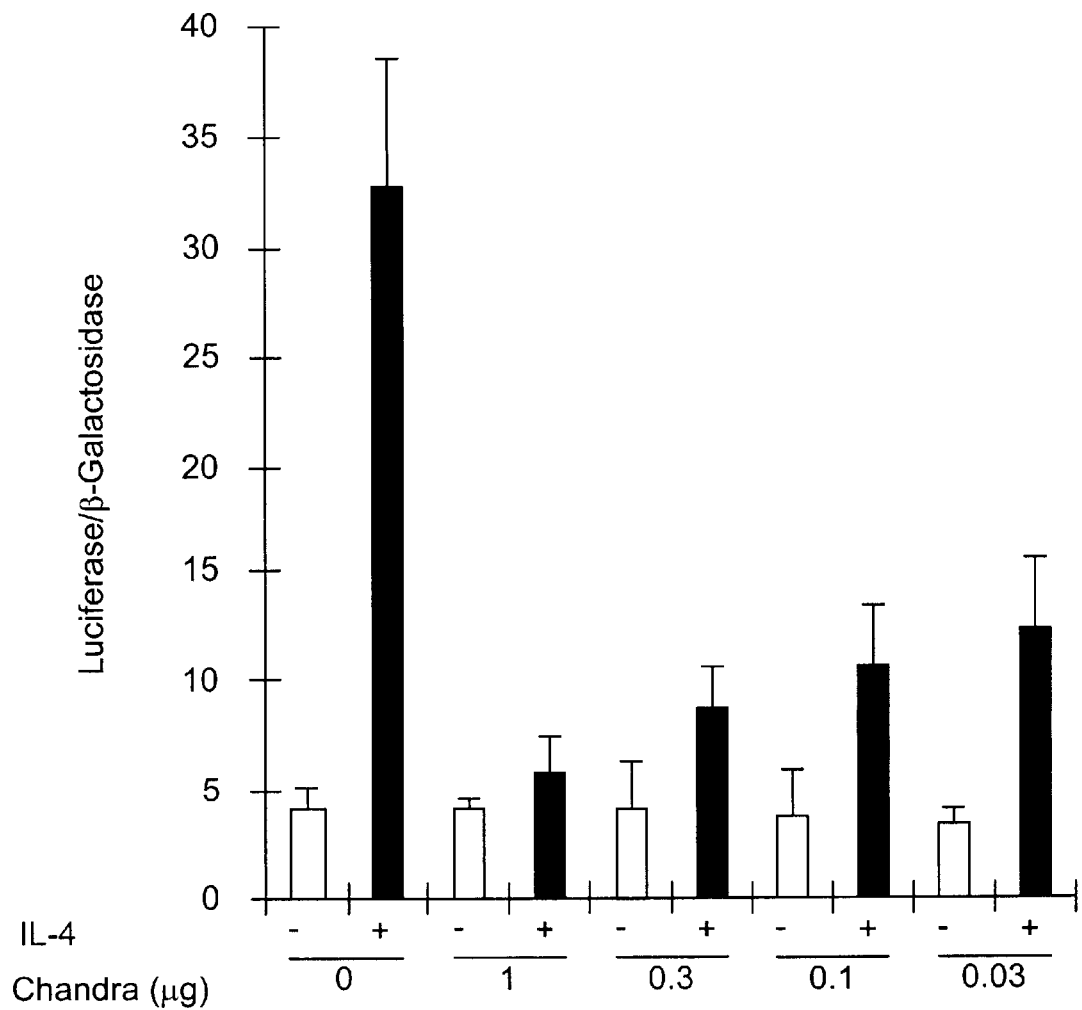

PKVLGVLQVM IAIINLSLGI IILTTLFSEL PTSVMLMVPI  80
<u>          TM1                            </u>   <u>       </u>
                                              TM2
WGSIMFIVSG SLSIAAGVTP TKCLIVASLT LNTITSVLAA 120
<u>         </u>                                <u>          </u>
   TM2                                         TM3
TASIMGVVSV AVGSQFPFRY NYTITKGLDV LMLIFNMLEF 160
<u>                   </u>                       <u>     </u>
        TM3                                     TM4
CLAVSVSAFG CEASCCNSRE VLVVLPSNPV ETVMAPPMTL 200
<u>        </u>
   TM4
QPLLPSEHQG TNVPGNVYKN HPGEIV                226

FIG. 1

SEQUENCE LISTING

<160> NUMBER OF SEQ ID NOS: 5

<210> SEQ ID NO 1
<211> LENGTH: 226
<212> TYPE: PRT
<213> ORGANISM: Mus sp.
<220> FEATURE:
<223> OTHER INFORMATION: Th1 cell-specific protein Chandra

<400> SEQUENCE: 1

| | | | | | | | | | | | | | | | |
|---|---|---|---|---|---|---|---|---|---|---|---|---|---|---|---|
| Met | Gln | Gly | Gln | Glu | Gln | Thr | Thr | Met | Ala | Val | Val | Pro | Gly | Val | Ala |
| 1 | | | | 5 | | | | | 10 | | | | | 15 | |
| Val | Pro | Ser | Lys | Asn | Ser | Val | Met | Thr | Ser | Gln | Met | Trp | Asn | Glu | Lys |
| | | | 20 | | | | | 25 | | | | | 30 | | |
| Lys | Glu | Lys | Phe | Leu | Lys | Gly | Glu | Pro | Lys | Val | Leu | Gly | Val | Leu | Gln |
| | | 35 | | | | | 40 | | | | | 45 | | | |
| Val | Met | Ile | Ala | Ile | Ile | Asn | Leu | Ser | Leu | Gly | Ile | Ile | Ile | Leu | Thr |
| 50 | | | | | 55 | | | | | 60 | | | | | |
| Thr | Leu | Phe | Ser | Glu | Leu | Pro | Thr | Ser | Val | Met | Leu | Met | Val | Pro | Ile |
| 65 | | | | 70 | | | | | 75 | | | | | 80 | |
| Trp | Gly | Ser | Ile | Met | Phe | Ile | Val | Ser | Gly | Ser | Leu | Ser | Ile | Ala | Ala |
| | | | | 85 | | | | | 90 | | | | | 95 | |
| Gly | Val | Thr | Pro | Thr | Lys | Cys | Leu | Ile | Val | Ala | Ser | Leu | Thr | Leu | Asn |
| | | | 100 | | | | | 105 | | | | | 110 | | |
| Thr | Ile | Thr | Ser | Val | Leu | Ala | Ala | Thr | Ala | Ser | Ile | Met | Gly | Val | Val |
| | | 115 | | | | | 120 | | | | | 125 | | | |
| Ser | Val | Ala | Val | Gly | Ser | Gln | Phe | Pro | Phe | Arg | Tyr | Asn | Tyr | Thr | Ile |
| 130 | | | | | 135 | | | | | 140 | | | | | |
| Thr | Lys | Gly | Leu | Asp | Val | Leu | Met | Leu | Ile | Phe | Asn | Met | Leu | Glu | Phe |
| 145 | | | | 150 | | | | | 155 | | | | | 160 | |
| Cys | Leu | Ala | Val | Ser | Val | Ser | Ala | Phe | Gly | Cys | Glu | Ala | Ser | Cys | Cys |
| | | | | 165 | | | | | 170 | | | | | 175 | |
| Asn | Ser | Arg | Glu | Val | Leu | Val | Val | Leu | Pro | Ser | Asn | Pro | Val | Glu | Thr |
| | | | 180 | | | | | 185 | | | | | 190 | | |
| Val | Met | Ala | Pro | Pro | Met | Thr | Leu | Gln | Pro | Leu | Leu | Pro | Ser | Glu | His |
| | | 195 | | | | | 200 | | | | | 205 | | | |
| Gln | Gly | Thr | Asn | Val | Pro | Gly | Asn | Val | Tyr | Lys | Asn | His | Pro | Gly | Glu |
| 210 | | | | | 215 | | | | | 220 | | | | | |
| Ile | Val | | | | | | | | | | | | | | |
| 225 | | | | | | | | | | | | | | | |

<210> SEQ ID NO 2
<211> LENGTH: 1238
<212> TYPE: DNA
<213> ORGANISM: Mus sp.
<220> FEATURE:
<223> OTHER INFORMATION: chandra Th1 cDNA
<221> NAME/KEY: CDS
<222> LOCATION: (86)..(766)
<223> OTHER INFORMATION: Chandra protein

<400> SEQUENCE: 2

```
cacacaagca aagcttctcc tggaataaat cagctgacat ctgatccttt ccattgtctg      60
tactgtttct gctgctctgg aaaccatgca aggacaggaa cagaccacca tggcagtggt     120
tcctggagtt gctgtgcctt caaagaattc tgttatgaca tcacaaatgt ggaatgagaa     180
gaaagagaaa ttcttgaagg gggaacccaa agtccttggg gttttacaag tgatgattgc     240
```

-continued

```
tatcataaac ctcagcttag gaataataat tttgacaact ttattttctg aactacccac    300
ttcagtgatg ttaatggtcc caatttgggg atcaataatg ttcattgtct ccggatccct    360
gtccattgca gcaggagtga ctcctacaaa atgcctgatc gttgccagtc taactctgaa    420
cactatcacc tctgtgttgg ctgcaactgc aagcataatg ggtgtagtca gtgtggctgt    480
gggttcacag tttccgtttc ggtataatta tacaatcacc aagggtttgg atgttttgat    540
gttaattttc aatatgctag aattctgcct tgctgtgtcc gtctctgcat ttggatgtga    600
agcttcctgt tgtaactccc gtgaggttct tgtagtgcta ccatcaaatc ctgttgagac    660
agtgatggca cccccaatga cacttcaacc attgctacca tcagaacacc aagggaccaa    720
tgttccagga aatgtgtaca agaaccaccc aggagaaata gtctaatttt gatgtgtgtg    780
tgtgtgtatt tccctaggat attaacactt cattgcactg gcttttgagg tgaatattag    840
atttactgta agtatgtaag tcaagcactt attaggtcaa caacacttca acatattata    900
ttcattgtat gtacaagggg caatgaattt gcaaagatgt tttgaaagca aacagaaaaa    960
aaaaaaaaca accaaacaaa agacctctta gtgaaatgag gtctctttgc aaagactaaa   1020
aaactggagt tcacattttt gggggtgggg ggggcttttg ctaaataagt agatttagat   1080
gcttttgatc aagtacaaac tcataaagta tgtaagaaat tactaatgat aggaaccaat   1140
tttaatctca tatgtaacat agtgtataat ttaatagatc tggtaaaaat ttataataaa   1200
gagaaatgcc tgaaaaaaaa aaaaaaaaaa aaaaaaa                             1238
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:sense
      internal primer for generating chandra probe

<400> SEQUENCE: 3

```
cccacttcag tgatgttaat ggtc                                              24
```

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:antisense
      internal primer for generating chandra probe

<400> SEQUENCE: 4

```
caaatcctgt tgagacagtg atggc                                             25
```

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence:anti-DYKDDDDK
      epitope tag

<400> SEQUENCE: 5

```
Asp Tyr Lys Asp Asp Asp Asp Lys
  1               5
```

CHANDRA: A TH1-SPECIFIC GENE

This application claims the benefit of U.S. Provisional Application No. 60/161,201, filed Oct. 22, 1999, the disclosure of which is incorporated by reference.

BACKGROUND OF THE INVENTION

In response to infection, numerous cell types within the vertebrate immune system act in concert to effect the rapid and efficient clearance of the invading pathogen. Among these cell types are T cells, which develop in the thymus and which are responsible for cell-mediated immunity. T cells are divided into several major subclasses, including cytotoxic T cells, which kill virus-infected cells, as well as two classes of regulatory cells, called helper T cells (Th cells) and suppressor T cells, which act to modulate the activity of other immune cells. During chronic infections, helper T cells develop into at least two phenotypically and functionally distinct effector populations, Th1 and Th2 lymphocytes. Th1 cells produce IFN-γ and IL-2, which are commonly associated with cell-mediated immune responses against various intracellular pathogens, whereas Th2 cells produce cytokines such as IL-4, IL-5, IL-6, IL-10 and IL-13, which are crucial to control extracellular helminthic infections.

In certain cases, the number, activity, or other properties of Th1 or Th2 cells can become abnormal, and these cell types can play a role in one or another disease or condition. For example, Th1 cells have been associated with organ-specific autoimmune diseases, delayed-type hypersensitivity, and transplant rejection. In addition, imbalance of Th2 cytokines are observed in various atopic and allergic diseases, which are usually accompanied by increased production of IgG1 and IgE as well as the activation of eosinophils and mast cells.

Cytokines such as IL-12 and IL-4 have dominant roles in determining the outcome of Th differentiation into Th1 and Th2 subsets, respectively. These cytokines bind to their cognate receptors, leading to activation of the Janus family of kinases (JAKs) and the latent transcription factors known as signal transducers and activators of transcription (STATs). For example, in Th1 cells, following the binding of IL-12 to its cognate receptor, STAT4 is activated, thereby leading to the production of IFN-γ. Accordingly, STAT4-deficient mice are defective in Th1 differentiation and do not respond to intracellular pathogens such as Listeria monocytogenes. In Th2 cells, IL-4 leads to the activation of STAT6, which is essential for the development of these cells. Accordingly, STAT6-deficient mice have an impaired ability to produce IL-4-secreting Th2 cells, thereby resulting in a failure to expel intestinal helminths. Interestingly, these STAT6 mutant mice are protected from antigen-induced airway hyperresponsiveness.

Additional reports have identified various genes that are differentially expressed in Th1 and Th2 cells. For example, the transcription factor ERM is selectively expressed in Th1 cells, and, in Th2 cells, GATA-3 and c-Maf are selectively expressed. GATA-3 is required for the expression of certain Th2 specific genes, can lead to the expression of IL-4 and IL-5 in Th1 cells, and inhibits the production of IFN-γ in Th1 cells. See, e.g., Zheng and Flavell (1997) *Cell* 89(4):587–96; Zhang et al., (1997) *J. Biol. Chem.* 272:21597–603; or Ferber et al., (1999) *Clin. Immunol.* 91:134–144. Additionally, several cell surface proteins are also differentially expressed in the Th1 and Th2 subsets. For example, Th1 cells express various chemokine receptors such as CXCR3, CCR1, and CCR5. Th2 cells, in contrast, express CD30 as well as various chemokine receptors such as CCR8.

Various cell surface proteins have been identified as having four-transmembrane domains, and are called tetraspanins, or transmembrane 4 superfamily (TM4SF). Such proteins, including, for example, CD81, CD9, and CD20, have a strong propensity to form molecular associations with other cell surface molecules. CD81, for example, which is expressed in both T and B lymphocytes, is found in a multimolecular complex with CD19 and the complement receptors 1 and 2 in B lymphocytes. Previous studies have demonstrated that this complex collectively regulates the threshold for antigen receptor-mediated B cell activation. In T cells, CD81 contributes to cell proliferation as well as to IL-2 and IL-4 production. Other four transmembrane proteins have been associated with various cellular activities, including receptor activity, cell-cell binding, integrin binding and/or signaling, or channel activity, e.g., $Ca^{2+}$ channel activity (see, e.g., Bubien et al., (1993) *J Cell Biol* 121(5): 1121–32).

SUMMARY OF THE INVENTION

The present invention provides nucleic acids encoding a novel Th1 cell-specific protein, Chandra. The herein-disclosed sequences can be used for any of a number of purposes, including for the specific detection of Th1 lymphocytes, for the identification of molecules that associate with and/or modulate the activity of Chandra, to diagnose any of a number of conditions associated with Th1 or Th2 cell activity, or to modulate the number and/or activity of Th1 or Th2 lymphocytes in a mammal.

In one aspect, the present invention provides isolated nucleic acids encoding a Th1-associated polypeptide, the polypeptide comprising at least about 70% amino acid sequence identity to SEQ ID NO:1.

In one embodiment, the polypeptide specifically binds to polyclonal antibodies generated against a polypeptide having an amino acid sequence of SEQ ID NO:1. In another embodiment, the polypeptide comprises an amino acid sequence of SEQ ID NO:1. In another embodiment, the nucleic acid hybridizes under moderately stringent hybridization conditions to a nucleic acid comprising a nucleotide sequence of SEQ ID NO:2. In another embodiment, the nucleic acid hybridizes under stringent hybridization conditions to a nucleic acid comprising a nucleotide sequence of SEQ ID NO:2.

In another aspect, the present invention provides an expression cassette comprising a nucleic acid encoding a Th1-associated polypeptide, the polypeptide comprising at least about 70% amino acid sequence identity to SEQ ID NO:1.

In another aspect, the present invention provides an isolated cell comprising the expression cassette.

In another aspect, the present invention provides an isolated polypeptide comprising at least about 70% amino acid sequence identity to SEQ ID NO:1.

In one embodiment, the polypeptide specifically binds to polyclonal antibodies generated against a polypeptide comprising an amino acid sequence of SEQ ID NO:1. In another embodiment, the polypeptide comprises an amino acid sequence of SEQ ID NO:1.

In another aspect, the present invention provides antibodies that specifically bind to a polypeptide comprising at least about 70% amino acid sequence identity to SEQ ID NO:1.

In another aspect, the present invention provides a method of identifying a compound that modulates Th1 cell activity or differentiation, the method comprising: (1) contacting a Th1-associated polypeptide with a compound, wherein the polypeptide comprises at least about 70% amino acid sequence identity to SEQ ID NO:1; and (2) determining the functional effect of the compound on the polypeptide.

In one embodiment, the polypeptide is expressed within a cell or a cell membrane. In another embodiment, the compound increases the activity of the polypeptide. In another embodiment, the compound decreases the activity of the polypeptide.

In another aspect, the present invention provides a method of treating a disease or a condition associated with Th1 cell activity in a patient, the method comprising administering to the patient a compound that decreases the activity of a Th1-associated polypeptide, the polypeptide comprising at least about 70% amino acid sequence identity to SEQ ID NO:1.

In a preferred embodiment, the compound is identified by (1) contacting the polypeptide with a compound, and (2) determining the functional effect of the compound on the polypeptide.

In one embodiment, the disease or condition is an autoimmune disease or transplant rejection.

In another aspect, the present invention provides a method of treating a disease or a condition associated with Th2 cell activity in a patient, the method comprising administering to the patient a compound that increases the activity of a Th1-associated polypeptide, the polypeptide comprising at least about 70% amino acid sequence identity to SEQ ID NO:1.

In a preferred embodiment, the compound is identified by (1) contacting the polypeptide with a compound, and (2) determining the functional effect of the compound on the polypeptide.

In one embodiment, the disease or condition is selected from the group consisting of allergy, asthma, and atopic diseases.

In another aspect, the present invention provides a method of treating a disease or condition associated with Th1 cell activity in a patient, the method comprising administering to the patient an antibody that specifically binds to a polypeptide comprising at least about 70% amino acid sequence identity to SEQ ID NO:1.

BRIEF DESCRIPTION OF THE DRAWINGS

FIG. 1 shows the amino acid sequence of the full-length Chandra protein (SEQ ID NO:1). The four potential transmembrane regions (TM) are underlined. Numbers on the right refer to amino acid residues.

FIG. 2 shows that Chandra overexpression inhibits IL-4 induced transcription. Jurkat T cells were transfected with an IL-4 inducible reporter construct along with indicated amounts of expression plasmid encoding Chandra and treated with IL-4. Luciferase and β-galactosidase activities were determined. The mean values and SDs of a total of three independent transfections are shown.

DETAILED DESCRIPTION OF THE INVENTION AND PREFERRED EMBODIMENTS

I. Introduction

The present invention provides nucleic acids encoding a novel Th1 specific protein. These nucleic acids and the proteins they encode are referred to as "chandra" polynucleotides and "Chandra" polypeptides. In some circumstances, "Chandra" can be used to refer to Chandra gene expression or activity in general, i.e., to any form of Chandra, including, e.g., genomic DNA, mRNA, polypeptides, etc. "Chandra" proteins are specifically expressed in Th1 lymphocytes, can act to promote Th1 cell differentiation and production, and can inhibit Th2 cell differentiation and production. In particular, Chandra can be used to inhibit IL-4 activity in Th2 cells. Chandra proteins and nucleic acids can also be used as a specific marker to identify Th1 cells, and to modulate the number and/or activity of Th1 or Th2 cells in a mammal. Accordingly, the present methods can be used to treat any of a number of diseases or conditions associated with Th1 or Th2 cell activity.

The invention also provides methods of screening for modulators, e.g., activators, inhibitors, stimulators, enhancers, etc., of Chandra nucleic acids and proteins. Such modulators can affect Chandra activity, e.g., by modulating Chandra transcription, translation, mRNA or protein stability; by altering the binding of Chandra to heterologous proteins, to the plasma membrane, or to other molecules; or by affecting Chandra protein activity. Such modulators of Chandra activity are thus useful for the pharmacological and genetic modulation of Th1 and/or Th2 cell number or activity, and, accordingly, for the treatment of any of a number of diseases associated with Th1 or Th2 lymphocytes. In one embodiment, compounds are screened, e.g., using high throughput screening (HTS), to identify those compounds that can bind to and/or modulate the activity of an isolated Chandra polypeptide or fragment thereof. In another embodiment, Chandra proteins are recombinantly expressed in cells, and the modulation of Chandra is assayed by measuring the number of Th1 and/or Th2 cells, or by detecting any measure of Th1 or Th2 cell activity and/or presence. For example, for Th1 cells, expression of interferon gamma (IFN-γ) or IL-2 can be measured, or, for Th2 cells, expression of IL-4, IL-5, IL-6, IL-10, or IL-13 is detected.

In numerous embodiments, a Chandra polynucleotide or polypeptide is ntroduced into a cell, in vivo or ex vivo, and the Chandra activity in the cell is thereby modulated. For example, a polynucleotide encoding a full length Chandra polypeptide can be introduced into a population of cells, thereby promoting the Th1 differentiation, and inhibiting the Th2 differentiation, of the cells. Alternatively, an antisense, ribozyme, or dominant-negative encoding polynucleotide can be introduced into a population of cells, thereby inhibiting the Th1 differentiation, and promoting the Th2 differentiation, of the cells.

In certain embodiments, monoclonal or polyclonal antibodies directed to Chandra, preferably an N-terminal domain, C-terminal domain, or extracellular loop of Chandra, will be administered to a mammal to inhibit the activity of Chandra in Th1 cells. Such embodiments are useful, e.g., in the treatment of a disease or disorder associated with Th1 cells, such as an autoimmune disease or transplant rejection.

The present invention also provides methods for detecting Chandra nucleic acid and protein expression, allowing investigation into Th1 cell regulation and allowing the specific identification of Th1 cells. chandra also provides useful nucleic acid probes for paternity and forensic investigations. Chandra polypeptides can also be used to generate monoclonal and polyclonal antibodies useful for identifying Th1 cells. Th1 cells can also be identified using techniques such as reverse transcription and amplification of mRNA, isolation of total RNA or poly $A^+$ RNA, northern blotting, dot blotting, in situ hybridization, RNase protection, S1 digestion, probing DNA microchip arrays, western blots, and the like.

Functionally, chandra nucleic acids encode membrane associated proteins that are expressed specifically in Th1 cells, and which contribute to the Th1 phenotype. In particular, Chandra acts to downregulate IL-4 signaling in T cells, thereby promoting Th1 differentiation and inhibiting Th2 cell differentiation. Structurally, the nucleotide sequence of chandra (see, e.g., SEQ ID NO:2, isolated from mice) encodes polypeptides comprising an amino-terminal (N-terminal) domain, four transmembrane domains, and a C-terminal domain. Related chandra genes from other species share at least about 60% nucleotide sequence identity over a region of at least about 50 nucleotides in length, optionally 100, 200, 500, or more nucleotides in length, to SEQ ID NO:2, or encode polypeptides sharing at least about 60% amino acid sequence identity over an amino acid region at least about 25 amino acids in length, optionally 50 to 100 amino acids in length to SEQ ID NO:1.

The present invention also provides polymorphic variants of the Chandra protein depicted in SEQ ID NO:1: variant #1, in which an isoleucine residue is substituted for a valine residue at amino acid position 11; and variant #2, in which an alanine residue is substituted for a glycine residue at amino acid position 3.

Specific regions of the Chandra nucleotide and amino acid sequences may be used to identify polymorphic variants, interspecies homologs, and alleles of chandra genes. This identification can be made in vitro, e.g., under stringent hybridization conditions, or PCR and sequencing, or by using the sequence information in a computer system for comparison with other nucleotide sequences. Typically, identification of polymorphic variants and alleles of chandra is made by comparing an amino acid sequence of about 25 amino acids or more, e.g., 50–100 amino acids. Amino acid identity of approximately at least 60% or above, optionally 65%, 70%, 75%, 80%, 85%, or 90–95% or above typically demonstrates that a protein is a polymorphic variant, interspecies homolog, or allele of Chandra. Sequence comparison can be performed using any of the sequence comparison algorithms discussed below. Antibodies that bind specifically to Chandra polypeptides or a conserved region thereof can also be used to identify alleles, interspecies homologs, and polymorphic variants.

Polymorphic variants, interspecies homologs, and alleles of Chandra are confirmed by examining Th1 cell specific expression of the putative Chandra polypeptide. Typically, a Chandra polypeptide having an amino acid sequence of SEQ ID NO:1 is used as a positive control in comparison to the putative Chandra protein to demonstrate the identification of a polymorphic variant or allele of the Chandra gene or protein.

Nucleotide and amino acid sequence information for Chandra may also be used to construct models of Th1 cell specific polypeptides in a computer system. These models are subsequently used to identify compounds that can activate or inhibit Chandra proteins. Such compounds that modulate the activity of Chandra genes or proteins can be used to investigate the role of chandra genes in Th1 cell polarization.

The present invention also provides assays, preferably high throughput assays, to identify compounds or other molecules that interact with and/or modulate Chandra. In certain assays, a particular domain of Chandra is used, e.g., an N-terminal, transmembrane, extracellular loop, or C-terminal domain.

The present invention also provides methods to treat diseases or conditions associated with Th1 or Th2 cell polarization. For example, Chandra activity and/or expression can be altered in cells of a patient with a Th2-associated disease or condition, such as allergy, asthma, and atopic diseases. In such patients, the expression and/or activation of Chandra in Th2 cells will drive the cells away from Th2 polarization and towards a Th1 state, thereby providing a treatment for the disorder. In addition, Chandra activity and/or expression can be inhibited in cells of a patient with a Th1-mediated disease or condition, such as autoimmune diseases and transplant rejection.

II. Definitions

As used herein, the following terms have the meanings ascribed to them unless specified otherwise.

"Th1 cells" refer to a subset of helper T cell lymphocytes that are characterized in terms of their patterns of gene expression and protein secretion, as well as their functional activity. For example, Th1 cells tend to synthesize IL-2 and IFN-γ, and to not synthesize IL-4, IL-5, IL-10, or IL-13. Th1 cells tend to be involved in, inter alia, cell-mediated immune responses against various intracellular pathogens, organ-specific autoimmune diseases, and delayed-type hypersensitivity. "Th1 cells" refer to cells with any one or more of the above characteristics.

"Th2 cells" refer to a subset of helper T cell lymphocytes that are characterized in terms of their patterns of gene expression and/or protein secretion, or by their functional activity. For example, Th2 cells tend to synthesize IL-4, IL-5, IL-6, IL-10, and IL-13. In addition, Th2 cells are involved in humoral immune responses, e.g., the control of extracellular helminthic infections. "Th2 cells" refer to cells with any one or more of the above characteristics.

As used herein, "Chandra" refers to a membrane bound protein as shown in SEQ ID NO:1, or any derivative, homolog, or fragment thereof, or to any nucleic acid encoding such a protein, derivative, homolog, or fragment thereof. Typically, Chandra is expressed specifically in Th1 cells, but Chandra proteins or derivatives can be expressed in any cell type, including any eukaryotic or prokaryotic cell, or synthesized in vitro. Typically, chandra nucleic acids encode a membrane-bound protein with four transmembrane regions. It will be recognized, however, that derivatives, homologs, and fragments of Chandra can be readily used in the present invention. Such Chandra variants can comprise any one or more of the domains of the polypeptide shown as SEQ ID NO:1, or multiple copies of any one or more domains, or any number of domains in novel combinations with each other or which other proteins or protein domains.

The term "Chandra" also refers to polymorphic variants, alleles, mutants, and interspecies homologs that: (1) have about 60% amino acid sequence identity, optionally about 75, 80, 85, 90, or 95% amino acid sequence identity to SEQ ID NO:1 over a window of about 25 amino acids, optionally 50–100 amino acids; (2) specifically bind to antibodies raised against an immunogen comprising an amino acid sequence of SEQ ID NO:1, and conservatively modified variants thereof; or (3) specifically hybridize (with a size of at least about 100, optionally at least about 500–1000 nucleotides) under stringent hybridization conditions to a sequence of SEQ ID NO:2, and conservatively modified variants thereof.

Topologically, full-length Chandra polypeptides are "W-shaped," with an "N-terminal domain," four "transmembrane domains," an "extracellular loop," two "cytoplasmic loops," and a "C-terminal domain." These domains can be structurally identified using methods known to those of skill in the art, such as sequence analysis programs that identify hydrophobic and hydrophilic domains (see, e.g. Stryer, Biochemistry ($3^{rd}$ ed. 1988); see also any of a number of Internet based sequence analysis programs, such as those found at dot.imgen.bcm.tmc.edu).

"Extracellular loop" refers to the portion of Chandra, located between the second and third transmembrane domains, that protrudes from the cellular membrane and is exposed to the extracellular face of the cell.

The "N-terminal domain" starts at the N-terminus and extends to a region close to the start of the first transmembrane domain, and the "C-terminal domain" region starts at the end of the last, e.g., the fourth, transmembrane domain and extends to the end of the polypeptide chain.

"Transmembrane domain" refers to a hydrophobic protein domain that lies within and spans the plasma membrane, and may also include the corresponding cytoplasmic (intracellular) and extracellular loops. The four transmembrane domains of Chandra can be identified using standard methods, as described in Kyte & Doolittle, *J. Mol. Biol.* 157:105–132 (1982)), or in Stryer, supra.

"Cytoplasmic loop" refers to the regions between the first and second, and third and fourth, transmembrane domains of a full-length Chandra protein. "Cytoplasmic loops" face the intracellular, or cytoplasmic, side of the cell membrane.

"Biological sample," as used herein, refers to a sample of biological tissue or fluid that contains one or more chandra nucleic acids encoding one or more Chandra proteins. Such samples include, but are not limited to, tissue isolated from humans, mice, and rats, in particular, blood, lymphatic tissue, liver, brain, heart, lung, spleen, testis, ovary, thymus, kidney, embryonic tissues. Biological samples may also include sections of tissues such as frozen sections taken for histological purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as a chimpanzee or a human.

By "determining the functional effect" is meant assaying for a compound that modulates, e.g., increases or decreases, a parameter that is indirectly or directly under the influence of a Chandra polypeptide, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, changes in gene expression of chandra or any Th1 or Th2-associated genes, or of any marker genes, and the like.

"Inhibitors," "activators," and "modulators" of Chandra genes or proteins are used interchangeably to refer to inhibitory, activating, or modulating molecules identified using in vitro and in vivo assays for Th1 and/or Th2 cell polarization or number. Inhibitors are compounds that, e.g., bind to Chandra proteins, partially or totally block Chandra activity, downregulate Chandra expression or stability, or prevent Chandra binding to membranes or to any other protein or factor. Activators are compounds that, e.g., bind to Chandra, stimulate Chandra activity, increase Chandra expression or stability, or facilitate Chandra binding to membranes or to any other protein or factor. Modulators may include genetically modified versions of Chandra proteins, e.g., dominant negative or activated forms of Chandra. Such assays for inhibitors and activators are described below and include, e.g., expressing Chandra proteins in cells or cell membranes, applying putative modulator compounds, and then determining the functional effects on Th1 cell polarization. Samples or assays comprising Chandra polypeptides that are treated with a potential activator, inhibitor, or modulator are compared to control samples without the inhibitor, activator, or modulator to examine the effect of the candidate compound. Control samples (untreated with the compound) are assigned a relative Chandra activity value of 100%. Inhibition of a Chandra polypeptide is achieved when the activity value relative to the control is about 80%, optionally 50% or 25–0%. Activation of a Chandra polypeptide is achieved when the activity value relative to the control is 110%, optionally 150%, optionally 200–500%, or 1000–3000% higher.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated chandra nucleic acid is separated from open reading frames that flank the chandra gene and encode proteins other than Chandra. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of finctionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I: The Conformation of Biological Macromolecules* (1980).

"Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source.

Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a finctional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 50 amino acids or nucleotides in length, or more preferably over a region that is 75–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:244 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387–395 (1984)).

Another example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. Software for perforning BLAST analyses is publicly available through the National Center for Biotechnology Information and can be found on the worldwide web at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such washes can be performed for 5, 15, 30, 60, 120, or more minutes.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-Chandra" antibody is an antibody or antibody fragment that specifically binds a polypeptide encoded by a chandra gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a Chandra polypeptide from specific species such as rat, mouse, or human can be selected to obtain only those polyclonal antibodies that are specifically immunoreactive with the Chandra protein and not with other proteins, except for polymorphic variants and alleles of the Chandra protein. This selection may be achieved by subtracting out antibodies that cross-react with Chandra molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as *E. coli,* or eukaryotic cells such as yeast, insect, amphibian, or mammalian cells such as CHO, HeLa and the like, e.g., cultured cells, explants, and cells in vivo.

III. Manipulation and Detection of Chandra Nucleic Acids

In numerous embodiments of the present invention, nucleic acids encoding a Chandra polypeptide, including a full-length Chandra protein, or any derivative, variant, homolog, or fragment thereof, will be used. Such nucleic acids are useful for any of a number of applications, including for the production of Chandra protein, for diagnostic assays, for therapeutic applications, for Chandra and/or Th1 cell specific probes, for assays for Chandra binding and/or modulating compounds, to identify and/or isolate Chandra homologs from other species or from mice, and other applications.

A. General Recombinant DNA Methods

Numerous applications of the present invention involve the cloning, synthesis, maintenance, mutagenesis, and other manipulations of nucleic acid sequences that can be performed using routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Isolating and Detecting Chandra Nucleotide Sequences

In numerous embodiments of the present invention, Chandra nucleic acids will be isolated and cloned using recombinant methods. Such embodiments are used, e.g., to isolate chandra polynucleotides for protein expression or during the generation of variants, derivatives, expression cassettes, or other sequences derived from chandra, to monitor chandra gene expression, for the determination of chandra sequences in various species, for diagnostic purposes in a patient, i.e., to detect mutations in chandra, or for genotyping and/or forensic applications.

Often, the nucleic acid sequences encoding Chandra proteins and related nucleic acid sequence homologs are cloned from cDNA and genomic DNA libraries by hybridization with probes, or isolated using amplification techniques with oligonucleotide primers. For example, chandra sequences are typically isolated from mammalian nucleic acid (genomic or cDNA) libraries by hybridizing with a nucleic acid probe, the sequence of which can be derived from SEQ ID NO:2, or amplified using primers comprising SEQ ID NOs: 3 and 4. A suitable biological material from which RNA and cDNA for Chandra can be isolated is blood, lymph, brain, liver, heart, lung, spleen, testis, ovary, thymus, kidney or other tissues.

Amplification techniques using primers can also be used to amplify and isolate chandra sequences from DNA or RNA (see, e.g., Dieffenfach & Dveksler, *PCR Primer: A Laboratory Manual* (1995)). Primers can be used, e.g., to amplify either the full length sequence or a probe of from one to several hundred nucleotides (using, e.g., primers shown as SEQ ID NOs: 3 and 4), which is then used to screen a mammalian library for full-length chandra clones.

Nucleic acids encoding Chandra polypeptides can also be isolated from expression libraries using antibodies as probes. Such polyclonal or monoclonal antibodies can be raised using the sequence of SEQ ID NO:1, or derivatives or fragments thereof.

Polymorphic variants, alleles, and interspecies homologs that are substantially identical to a chandra gene can be isolated using chandra nucleic acid probes, and oligonucleotides under stringent hybridization conditions, by screening libraries. Alternatively, expression libraries can be used to clone chandra polymorphic variants, alleles, and interspecies homologs, by detecting expressed homologs immunologically with antisera or purified antibodies made against a Chandra polypeptide, which also recognize and selectively bind to the Chandra homolog.

More distantly related chandra homologs can be identified using any of a number of well known techniques, including by hybridizing a chandra probe with a genomic or cDNA library using moderately stringent conditions, or under low stringency conditions. Also, a distant homolog can be amplified from a nucleic acid library using degenerate primer sets, ie., primers that incorporate all possible codons encoding a given amino acid sequence, in particular based on a highly conserved amino acid stretch. Such primers are well known by those of skill, and numerous programs are available, e.g., on the internet, for degenerate primer design.

To make a cDNA library, one should choose a source that is rich in chandra mRNA, e.g., cells isolated from blood, lymphatic tissue, liver, brain, heart, lung, spleen, testis, ovary, thymus, kidney, or embryonic tissue. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffmnan, *Gene* 25:263–269 (1983); Sambrook et al., supra; Ausubel et al., supra).

For a genomic library, the DNA is extracted from the tissue or cells and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA*, 72:3961–3965 (1975).

An alternative method of isolating chandra nucleic acid and its homologs combines the use of synthetic oligonucleotide primers and amplification of an RNA or DNA template (see, U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of chandra genes directly from mRNA, from cDNA, from genomic libraries or cDNA libraries. Degenerate oligonucleotides can be designed to amplify chandra homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of Chandra-encoding mRNA in physiological samples, for nucleic acid sequencing, or for other purposes. Genes amplified by the PCR reaction can be purified from agarose gels and cloned into an appropriate vector.

Synthetic oligonucleotides can be used to construct recombinant chandra genes for use as probes or for expression of protein. This method is performed using a series of overlapping oligonucleotides usually 40–120 bp in length, representing both the sense and non-sense strands of the gene. These DNA fragments are then annealed, ligated and cloned. Alternatively, amplification techniques can be used with precise primers to amplify a specific subsequence of the chandra nucleic acid. The specific subsequence is then ligated into an expression vector.

The nucleic acid encoding a Chandra polypeptide is typically cloned into intermediate vectors before transformation into prokaryotic or eukaryotic cells for replication and/or expression. These intermediate vectors are typically prokaryote vectors, e.g., plasmids, or shuttle vectors. Vectors, cells, and transfection methods are well known to those of skill and are described, e.g., in Ausubel or in Sambrook, both supra.

Optionally, nucleic acids will be used that encoding chimeric proteins comprising a Chandra polypeptide or domains thereof in combination with a heterologous polypeptide or polypeptides. For example, a domain such as an N-terminal or C-terminal domain, an extracellular loop, or a transmembrane domain of Chandra can be covalently linked to a heterologous protein such as a heterologous transmembrane domain or a heterologous extracellular domain. Other heterologous proteins of choice include, e.g., luciferase, green fluorescent protein (GFP), and β-gal.

In certain embodiments, chandra polynucleotides will be detected using hybridization-based methods to determine, e.g., chandra RNA levels or to detect particular DNA sequences, e.g., for genotyping or for forensic applications. For example, gene expression of chandra can be analyzed by techniques known in the art, e.g., Northern blotting, reverse transcription and amplification of mRNA, dot blotting, in situ hybridization, RNase protection, probing DNA microchip arrays, and the like. In one embodiment, high density oligonucleotide analysis technology (e.g., GeneChip™) is used to identify homologs and polymorphic variants of chandra, or to monitor levels of chandra mRNA. In the case where a homologs is linked to a known disease, they can be used with GeneChip™ as a diagnostic tool in detecting the disease in a biological sample, see, e.g., Gunthand et al., *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

In certain applications, a chandra DNA sequence will be detected, e.g., for diagnostic or forensic applications. For example, a chandra allele can be detected in a mammal using Southern blot hybridization, i.e., by isolating genomic DNA, performing a restriction digest on the isolated DNA, separating the restriction fragments electrophoretically, e.g., in an agarose gel, and transferring the separated DNA to a membrane and probing with a specific, labeled sequence. Southern blotting is well known to those of skill, and is taught in numerous sources, including Ausubel et al. and Sambrook et al.

In other embodiments, e.g., to detect tissue specific or temporal patterns of gene expression, a chandra polynucleotide is detected using in situ hybridization. In in situ hybridization, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology,* vol. VII, pp. 189–226 (1984); and *Nucleic Acid Hybridization: A Practical Approach* (Hames et al., eds. 1987).

C. Expression in Prokaryotes and Eukaryotes

Often, a cloned chandra sequence will be expressed in a prokaryotic or eukaryotic cell to obtain expression, i.e., production of the encoded mRNA or protein. In addition, in numerous embodiments, a chandra polynucleotide will be introduced into a cell to modulate the level of Chandra activity in the cell, and thereby modulate the number or properties of Th1 or Th2 cells in a patient. To obtain high level expression of a cloned gene or nucleic acid, such as a cDNA encoding a Chandra polypeptide, a chandra sequence is typically subcloned into an expression vector that contains a strong promoter to direct transcription, a transcription/translation terminator, and if for a nucleic acid encoding a protein, a ribosome binding site for translational initiation. Suitable bacterial promoters are well known in the art and are described, e.g. in Sambrook et al. and Ausubel et al. Bacterial expression systems for expressing the Chandra protein are available in, e.g., *E. coli,* Bacillus sp., and Salmonella (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

For therapeutic applications, chandra nucleic acids are introduced into a cell, in vitro, in vivo, or ex vivo, using any of a large number of methods including, but not limited to, infection with viral vectors, liposome-based methods, biolistic particle acceleration (the gene gun), and naked DNA injection. Such therapeutically useful nucleic acids include, but are not limited to, coding sequences for full-length Chandra, coding sequences for a Chandra fragment, domain, derivative, or variant, chandra antisense sequences, and chandra ribozymes. Typically, such sequences will be operably linked to a promoter, but in numerous applications a nucleic acid will be administered to a cell that is itself directly therapeutically effective, e.g., certain antisense or ribozyme molecules.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the Chandra-encoding nucleic acid in host cells. A typical expression cassette thus contains a promoter operably linked to the nucleic acid sequence encoding a Chandra polypeptide, and signals required for efficient polyadenylation of the transcript, ribosome binding sites, and translation termination. The nucleic acid sequence encoding a Chandra polypeptide may be linked to a cleavable signal peptide sequence to promote secretion of the encoded protein by the transfected cell. Such signal peptides would include, among others, the signal peptides from tissue plasminogen activator, insulin, and neuron growth factor, and juvenile hormone esterase of *Heliothis virescens.* Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, eg., c-myc, HA-tag, 6-His tag, maltose binding protein, VSV-G tag, anti-DYKDDDDK (SEQ ID NO:5) tag, or any such tag, a large number of which are well known to those of skill in the art.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/$A^+$, pMTO10/$A^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification, such as neomycin, thymidine kinase, hygromycin B phosphotransferase, and dihydrofolate reductase. Alternatively, high yield expression systems not involving gene amplification are also suitable, such as using a baculovirus vector in insect cells, with a sequence encoding a Chandra polypeptide under the direction of the polyhedrin promoter or other strong baculovirus promoters.

The elements that are typically included in expression vectors also include a replicon that functions in *E. coli,* a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of a Chandra protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of reagents such as Superfect (Qiagen), liposomes, calcium phosphate transfection, polybrene, protoplast fusion, electroporation, microinjection, plasmid vectors, viral vectors, biolistic particle acceleration (the gene gun), or any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing a chandra gene.

After the expression vector is introduced into the cells, the transfected cells are cultured under conditions favoring expression of the Chandra polypeptide, which is recovered from the culture using standard techniques identified below. Methods of culturing prokaryotic or eukaryotic cells are well known and are taught, e.g., in Ausubel et al., Sambrook et al., and in Freshney, *Culture of Animal Cells*, 3d. Ed., (1993), A Wiley-Liss Publication.

IV. Purification of Chandra Polypeptides

Either naturally occurring or recombinant Chandra polypeptides can be purified for use in functional assays, binding assays, diagnostic assays, and other applications. Optionally, recombinant Chandra polypeptides are purified. Naturally occurring Chandra polypeptides are purified, e.g., from mammalian tissue such as blood, lymphatic tissue, or any other source of a Chandra homolog. Recombinant Chandra polypeptides are purified from any suitable bacterial or eukaryotic expression system, e.g., CHO cells or insect cells.

Chandra proteins may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant Chandra polypeptide is being purified. For example, proteins having established molecular adhesion properties can be reversibly fused to the Chandra polypeptide. With the appropriate ligand, a Chandra polypeptide can be selectively adsorbed to a purification column and then freed from the column in a relatively pure form. The fused protein is then removed by enzymatic activity. Chandra proteins can also be purified using immunoaffinity columns.

A. Purification of Chandra Protein from Recombinant Cells

Recombinant proteins are expressed by transformed bacteria or eukaryotic cells such as CHO cells or insect cells in large amounts, typically after promoter induction; but expression can be constitutive. Promoter induction with IPTG is one example of an inducible promoter system. Cells are grown according to standard procedures in the art. Fresh or frozen cells are used for isolation of protein.

Proteins expressed in bacteria may form insoluble aggregates ("inclusion bodies"). Several protocols are suitable for purification of Chandra inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Chandra polypeptides are separated from other bacterial proteins by standard separation techniques, e.g., with Ni-NTA agarose resin.

Alternatively, it is possible to purify Chandra polypeptides from bacteria periplasm. After lysis of the bacteria, when a Chandra protein is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Chandra Polypeptides

1. Solubility fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

2. Size differential filtration

The molecular weight of a Chandra protein can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column chromatography

Chandra proteins can also be separated from other proteins on the basis of its size, net surface charge, hydrophobicity, and affinity for heterologous molecules. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Antibodies to Chandra Family Members

In numerous embodiments of the present invention, antibodies that specifically bind to Chandra polypeptides will be used. Such antibodies have numerous applications, including for the modulation of Chandra activity and for inununoassays to detect Chandra, and variants, derivatives, fragments, etc. of Chandra. Immunoassays can be used to qualitatively or quantitatively analyze the Chandra polypeptide. A general overview of the applicable technology can be found in Harlow & Lane, *Antibodies: A Laboratory Manual* (1988).

Methods of producing polyclonal and monoclonal antibodies that react specifically with Chandra polypeptides are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of Chandra-comprising immunogens may be used to produce antibodies specifically reactive with a Chandra polypeptide. For example, a recombinant Chandra protein, or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the Chandra polypeptide. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-Chandra proteins, or even related proteins from other organisms, using a competitive binding immunoassay. Specific polyclonal antisera and monoclonal antibodies will usually bind with a $K_d$ of at least about 0.1 mM, more usually at least about 1 $\mu$M, optionally at least about 0.1 $\mu$M or better, and optionally 0.01 $\mu$M or better.

Once Chandra-specific antibodies are available, individual Chandra proteins can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

A. Immunological Binding Assays

Chandra proteins can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology,* volume 37 (Asai, ed. 1993); Basic and *Clinical Immunology* (Stites & Terr, eds., 7th ed. 1991). Immunological binding assays (or immunoassays) typically use an antibody that specifically binds to a protein or antigen of choice (in this case a Chandra protein or an antigenic subsequence thereof). The antibody (e.g., anti-Chandra) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled Chandra polypeptide or a labeled anti-Chandra antibody. Alternatively, the labeling agent may be a third moiety, such a secondary antibody, that specifically binds to the antibody/Chandra complex (a secondary antibody is typically specific to antibodies of the species from which the first antibody is derived). Other proteins capable of specifically binding immunoglobulin constant regions, such as protein A or protein G, may also be used as the label agent. These proteins exhibit a strong nonimmunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

1. Noncompetitive assay formats

Immunoassays for detecting a Chandra protein in a sample may be either competitive or noncompetitive. Noncompetitive immunoassays are assays in which the amount of antigen is directly measured. In one preferred "sandwich" assay, for example, the anti-Chandra antibodies can be bound directly to a solid substrate on which they are immobilized. These immobilized antibodies then capture the Chandra protein present in the test sample. The Chandra protein is thus immobilized is then bound by a labeling agent, such as a second Chandra antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

2. Competitive assay formats

In competitive assays, the amount of Chandra protein present in the sample is measured indirectly by measuring the amount of a known, added (exogenous) Chandra protein displaced (competed away) from an anti-Chandra antibody by the unknown Chandra protein present in a sample. In one competitive assay, a known amount of Chandra protein is added to a sample and the sample is then contacted with an antibody that specifically binds to the Chandra protein. The amount of exogenous Chandra protein bound to the antibody is inversely proportional to the concentration of Chandra protein present in the sample. In a particularly preferred embodiment, the antibody is immobilized on a solid substrate. The amount of Chandra protein bound to the antibody may be determined either by measuring the amount of Chandra protein present in a Chandra/antibody complex, or alternatively by measuring the amount of remaining uncomplexed protein. The amount of Chandra protein may be detected by providing a labeled Chandra molecule.

A hapten inhibition assay is another preferred competitive assay. In this assay the known Chandra protein is immobilized on a solid substrate. A known amount of anti-Chandra antibody is added to the sample, and the sample is then contacted with the immobilized Chandra. The amount of anti-Chandra antibody bound to the known immobilized Chandra protein is inversely proportional to the amount of Chandra protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

3. Cross-reactivity determinations

Immmunoassays in the competitive binding format can also be used for crossreactivity determinations. For example, a protein at least partially encoded by SEQ ID NO:2 can be immobilized to a solid support. Proteins (e.g., Chandra proteins and homologs) are added to the assay that compete for binding of the antisera to the immobilized antigen. The ability of the added proteins to compete for binding of the antisera to the immobilized protein is compared to the ability of the Chandra polypeptide encoded by SEQ ID NO:2 to compete with itself. The percent cross-reactivity for the above proteins is calculated, using standard calculations. Those antisera with less than 10% cross-reactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a Chandra protein, to the immunogen protein (i.e., Chandra protein encoded by SEQ ID NO:2). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:2 that is required to inhibit 50% of binding, then the second protein is said to specifically bind to the polyclonal antibodies generated to a Chandra immunogen.

Polyclonal antibodies that specifically bind to a Chandra protein from a particular species can be make by subtracting out cross-reactive antibodies using Chandra homologs. For example, antibodies specific to human Chandra can be made by subtracting out antibodies that are cross-reactive with mouse Chandra. In an analogous fashion, antibodies specific to a particular Chandra protein can be made in an organism with multiple chandra genes.

4. Other assay formats

Western blot (immunoblot) analysis is used to detect and quantify the presence of Chandra protein in a sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the Chandra protein. The anti-Chandra polypeptide antibodies specifically bind to the Chandra polypeptide on the solid support. These antibodies may be directly labeled or alternatively may be subsequently detected using labeled antibodies (e.g., labeled sheep anti-mouse antibodies) that specifically bind to the anti-Chandra antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

5. Reduction of nonspecific binding

One of skill in the art will appreciate that it is often desirable to minimize nonspecific binding in immunoassays. Particularly, where the assay involves an antigen or antibody immobilized on a solid substrate it is desirable to minimize the amount of nonspecific binding to the substrate. Means of reducing such nonspecific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

6. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Nonradioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize a Chandra protein, or secondary antibodies that recognize anti-Chandra.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Modulating Chandra Activity in Lymphocytes

A. Assays for Modulators of Chandra Proteins

In numerous embodiments of this invention, the level of Chandra activity will be modulated in a cell by administering to the cell, in vivo or in vitro, any of a large number of Chandra-modulating molecules, e.g., polypeptides, antibodies, amino acids, nucleotides, lipids, carbohydrates, or any organic or inorganic molecule.

To identify molecules capable of modulating Chandra, assays will be performed to detect the effect of various compounds on Chandra activity in a cell. Such assays can involve the identification of compounds that interact with Chandra proteins, either physically or genetically, and can thus rely on any of a number of standard methods to detect physical or genetic interactions between compounds. Such assays can also involve the detection of Th1 polarization in a cell, either in vitro or in vivo, and can thus involve the detection of Th1 or Th2 polarization using any standard assay, e.g., by measuring Th1 or Th2-specific markers, and the like. Such cell-based assays can be performed in any type of cell, e.g., a Th1 cell that naturally expresses Chandra or a cultured cell that produces Chandra due to recombinant expression.

B. Assays for Chandra-Interacting Compounds

In certain embodiments, assays will be performed to identify molecules that physically or genetically interact with Chandra proteins. Such molecules can be any type of molecule, including polypeptides, polynucleotides, amino acids, nucleotides, carbohydrates, lipids, or any other organic or inorganic molecule. Such molecules may represent molecules that normally interact with Chandra to effect Th1 polarization in lymphocytes, or may be synthetic or other molecules that are capable of interacting with Chandra and that can potentially be used to modulate Th1 and or Th2 polarization in cells, or used as lead compounds to identify classes of molecules that can interact with and/or modulate Chandra. Such assays may represent physical binding assays, such as affinity chromatography, immunoprecipitation, two-hybrid screens, or other binding assays, or may represent genetic assays as described infra.

In any of the binding or functional assays described herein, in vivo or in vitro, any Chandra protein, or any derivative, variation, homolog, or fragment of a Chandra protein, can be used. Preferably, the Chandra protein is at least about 70% identical to SEQ ID NO:1. In numerous embodiments, a fragment of a Chandra protein is used. For example, a fragment that contains only an N-terminal or C-terminal domain, an extracellular loop, or a transmembrane domain can be used. Such fragments can be used alone, in combination with other Chandra fragments, or in combination with sequences from heterologous proteins, e.g., the fragments can be fused to a heterologous polypeptide, thereby forming a chimeric polypeptide.

1. Assays for physical interactions

Compounds that interact with Chandra proteins can be isolated based on an ability to specifically bind to a Chandra protein or fragment thereof. In numerous embodiments, the Chandra protein or protein fragment will be attached to a solid support. In one embodiment, affinity columns are made using the Chandra polypeptide, and physically-interacting molecules are identified. It will be apparent to one of skill that chromatographic techniques can be performed at any scale and using equipment from many different manufacturers (e.g., Pharmacia Biotech). In addition, molecules that interact with Chandra proteins in vivo can be identified by co-immunoprecipitation or other methods, i.e., immunoprecipitating Chandra proteins using anti-Chandra antibodies from a cell or cell extract, and identifying compounds, e.g., proteins, that are precipitated along with the Chandra protein. Such methods are well known to those of skill in the art and are taught, e.g., in Ausubel et al., Sambrook et al., Harlow & Lane, all supra.

Two-hybrid screens can also be used to identify polypeptides that interact in vivo with a Chandra polypeptide or a fragment thereof (Fields et al., *Nature* 340:245–246 (1989)). Such screens comprise two discrete, modular domains of a transcription factor protein, e.g., a DNA binding domain and a transcriptional activation domain, which are produced in a cell as two separate polypeptides, each of which also comprises one of two potentially binding polypeptides. If the two potentially binding polypeptides in fact interact in vivo, then the DNA binding and the transcriptional activating domain of the transcription factor are united, thereby producing expression of a target gene in the cell. The target gene typically encodes an easily detectable gene product, e.g., β-galactosidase, GFP, or luciferase, which can be detected using standard methods. In the present invention, a Chandra polypeptide is fused to one of the two domains of the transcription factor, and the potential Chandra-binding polypeptides (e.g., encoded by a cDNA library) are fused to the other domain. Such methods are well known to those of skill in the art, and are taught, e.g., in Ausubel et al., supra.

C. Assays for Chandra Protein Activity chandra genes and their alleles and polymorphic variants encode membrane bound proteins that promote Th1 cell differentiation, and inhibit Th2 cell differentiation and associated IL-4 mediated gene expression. The activity of Chandra polypeptides can be assessed using a variety of in vitro and in vivo assays to determine functional, chemical, and physical effects, e.g., measuring the number or activity of Th1 and/or Th2 cells, measuring the expression or activity of Th1 or Th2 specific genes, e.g., IL-2 or IFN-γ for Th1 cells, or IL-4, IL-5, IL6, IL-10, or IL-13 for Th2 cells, measuring the binding of Chandra to heterologous proteins or other molecules (e.g., radioactive binding), measuring Chandra protein and/or RNA levels, or measuring other aspects of Chandra polypeptides, e.g., phosphorylation levels, transcription levels, receptor or channel activity, and the like. Such assays can be used to test for both activators and inhibitors of Chandra proteins. Modulators can also be genetically altered versions of Chandra proteins, e.g., dominant negative forms of Chandra or of proteins that interact with Chandra, e.g., IL-4 or components of the STAT/JAK pathway, or altered forms of Chandra-interacting proteins, e.g., IL-4. Such modulators of Th1 and Th2 cell differentiation and number are useful for, e.g., many diagnostic and therapeutic applications.

The Chandra protein of the assay will typically be a recombinant or naturally occurring polypeptide with a sequence of SEQ ID NO:1 or conservatively modified variant thereof. Alternatively, the Chandra protein of the assay will be derived from a eukaryote and include an amino acid subsequence having amino acid sequence identity to SEQ ID NO:1. Generally, the amino acid sequence identity will be at least 60%, optionally at least 70% to 85%, optionally at least 90–95%. Optionally, the polypeptide of the assays will comprise a domain of a Chandra protein, such as an N-terminal domain, a C-terminal domain, an extracellular loop, one or more transmembrane domains, and the like. In certain embodiments, a domain of a Chandra protein, e.g., an N-terminal domain, a C-terminal domain, an extracellular loop, or one or more transmembrane domains, is bound to a solid substrate and used, e.g., to isolate any molecules that can bind to and/or modulate their activity. In certain embodiments, a domain of a Chandra polypeptide, e.g., an N-terminal domain, a C-terminal domain, an extracellular loop, or one or more transmembrane domains, is fused to a heterologous polypeptide, thereby forming a chimeric polypeptide. Such chimeric polypeptides are also useful, e.g., in assays to identify modulators of Chandra.

Samples or assays that are treated with a potential Chandra protein inhibitor or activator are compared to control samples without the test compound, to examine the extent of modulation. Control samples (untreated with activators or inhibitors) are assigned a relative Chandra activity value of 100. Inhibition of a Chandra protein is achieved when the Chandra activity value relative to the control is about 90%, optionally 50%, optionally 25–0%. Activation of a Chandra protein is achieved when the Chandra activity value relative to the control is 110%, optionally 150%, 200–500%, or 1000–2000%.

The effects of the test compounds upon the function of the polypeptides can be measured by examining any of the parameters described above. Any suitable physiological change that affects Chandra activity can be used to assess the influence of a test compound on the polypeptides of this invention. When the functional consequences are determined using intact cells or animals, one can also measure a variety of effects such as changes in cell metabolism such as cell growth or pH changes, and changes in intracellular second messengers such as $Ca^{2+}$, IP3, cGMP, or cAMP.

In another embodiment, transcription levels can be measured to assess the effects of a test compound on Th1 or Th2 differentiation. A host cell containing a Chandra protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured using any method known to those of skill in the art to be suitable. For example, mRNA expression of the protein of interest may be detected using Northern blots or by detecting their polypeptide products using immunoassays. Any polynucleotide typically expressed in Th1 (e.g., IL-2 or IFN-γ) or Th2 cells (e.g., IL-4, IL-5, IL-6,IL-10, or IL-13) can be used. Alternatively, transcription based assays using reporter gene may be used as described in U.S. Pat. No. 5,436,128, herein incorporated by reference. The reporter genes can be, e.g., chloramphenicol acetyltransferase, luciferase, β-galactosidase and alkaline phosphatase Furthermore, the protein of interest can be used as an indirect reporter via attachment to a second reporter such as green fluorescent protein (see, e.g., Mistili & Spector, *Nature Biotechnology* 15:961–964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

D. Modulators and Binding Compounds

The compounds tested as modulators of a Chandra protein can be any small chemical compound, or a biological entity, such as a protein, sugar, nucleic acid or lipid. Alternatively, modulators can be genetically altered versions of a chandra gene. Typically, test compounds will be small chemical molecules and peptides. Essentially any chemical compound can be used as a potential modulator or binding compound in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one preferred embodiment, high throughput screening methods involve providing a combinatorial chemical or peptide library containing a large number of potential therapeutic compounds (potential modulator or binding compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g. U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

1. Solid state and soluble high throughput assays

In one embodiment, the invention provides soluble assays using molecules such as an N-terminal or C-terminal domain either alone or covalently linked to a heterologous protein to create a chimeric molecule. In another embodiment, the invention provides solid phase based in vitro assays in a high throughput format, where a domain, chimeric molecule, Chandra protein, or cell or tissue expressing a Chandra protein is attached to a solid phase substrate.

In the high throughput assays of the invention, it is possible to screen up to several thousand different modulators in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000–20,000 different compounds is possible using the integrated systems of the invention. More recently, microfluidic approaches to reagent manipulation have been developed.

The molecule of interest can be bound to the solid state component, directly or indirectly, via covalent or non covalent linkage, e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767–777 (1991); Sheldon et al., Clinical Chemistry 39(4):718–719 (1993); and Kozal et al., *Nature Medicine* 2(7):753759 (1996) (all describing arrays of biopolymers fixed to solid substrates). Nonchemical approaches for fixing tag binders to substrates include other common methods, such as heat, cross-linking by UV radiation, and the like.

2. Computer-based assays

Yet another assay for compounds that modulate Chandra protein activity involves computer assisted drug design, in which a computer system is used to generate a three-dimensional structure of a Chandra protein based on the structural information encoded by its amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind. These regions are then used to identify compounds that bind to the protein.

The three-dimensional structural model of the protein is generated by entering protein amino acid sequences of at least 10 amino acid residues or corresponding nucleic acid sequences encoding a Chandra polypeptide into the computer system. The nucleotide sequence encoding the polypeptide, or the amino acid sequence thereof, is preferably SEQ ID NO:2 or SEQ ID NO:1, and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential modulator binding regions are identified by the computer system. Three-dimensional structures for potential modulators are generated by entering amino acid or nucleotide sequences or chemical formulas of compounds, as described above. The three-dimensional structure of the potential modulator is then compared to that of the Chandra protein to identify compounds that bind to the protein. Binding affinity between the protein and compound is determined using energy terms to determine which compounds have an enhanced probability of binding to the protein.

Computer systems are also used to screen for mutations, polymorphic variants, alleles and interspecies homologs of chandra genes. Such mutations can be associated with disease states or genetic traits. As described above, Gene-Chip™ and related technology can also be used to screen for mutations, polymorphic variants, alleles and interspecies homologs. Once the variants are identified, diagnostic assays can be used to identify patients having such mutated genes. Identification of the mutated chandra genes involves receiving input of a first nucleic acid or amino acid sequence of SEQ ID NO:2 or SEQ ID NO:1, respectively, and conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various chandra genes, and mutations associated with disease states and genetic traits.

VII. Modulating Chandra Activity/expression to Treat Diseases or Conditions

In numerous embodiments of this invention, a compound, e.g., nucleic acid, polypeptide, or other molecule is administered to a patient, in vivo or ex vivo, to effect a change in Chandra activity or expression in the patient. Such compounds can be nucleic acids encoding full length Chandra polypeptides, e.g., as shown as SEQ D NO:1, or any derivative, fragment, or variant thereof, operably linked to a promoter. Suitable nucleic acids also include inhibitory sequences such as antisense or ribozyme sequences, which can be delivered in, e.g., an expression vector operably linked to a promoter, or can be delivered directly. Also, any nucleic acid that encodes a polypeptide that modulates the expression of Chandra can be used. In general, nucleic acids can be delivered to cells using any of a large number of vectors or methods, e.g., retroviral, adenoviral, or adeno-associated virus vectors, liposomal formulations, naked DNA injection, and others. All of these methods are well known to those of skill in the art.

Proteins can also be delivered to a patient to modulate Chandra activity. In preferred embodiments, a polyclonal or monoclonal antibody that specifically binds to Chandra, particularly to an N-terminal or C-terminal domain of a Chandra polypeptide, will be delivered. In addition, any polypeptide that interacts with and/or modulates Chandra activity can be used, e.g., a polypeptide that is identified using the presently described assays, or any dominant negative form of Chandra or a Chandra-interacting protein, e.g., IL-4, JAK3, STAT6, etc. Often, the protein used in such embodiments will interact with an extracellular portion of Chandra (e.g., a C-terminal domain, N-terminal domain, or extracellular loop). In addition, polypeptides that affect Chandra expression can be used.

Further, any compound that is found to or designed to interact with and/or modulate the activity of Chandra can be used. For example, any compound that is found, using the methods described herein, to bind to or modulate the activity of Chandra can be used.

Any of the above-described molecules can be used to increase or decrease the expression or activity of Chandra, or to otherwise affect the properties and/or behavior of Chandra polypeptides or polynucleotides, e.g., stability, intracellular localization, interactions with other intracellular or extracellular moieties, etc. The present compounds can thus be used to treat any disease or condition for which an increase or decrease in Th1 or Th2 cell activity or number would be beneficial. For example, any condition associated with or dependent on Th1 cells, such as autoimmune diseases or transplant rejection, can be treated using a compound that decreases Chandra expression and/or activity, thereby decreasing the number or activity of Th1 cells. Alternatively, conditions associated with or dependent on Th2 cells, such as allergies, atopic diseases, and asthma, can be treated using a compound that increases Chandra expression and/or activity, thereby inhibiting Th2 cell polarization, e.g., by inhibiting IL-4 or JAK/STAT activity. In addition, Chandra-activating compounds can be used to treat any disease or conditions for which Th1 cells play a protective or therapeutic role, e.g., Leishmania major infections. Similarly, Chandra inhibitors can be used to treat diseases or conditions for which Th2 cells play a beneficial role, e.g., helminthic infections.

A. Administration and Pharmaceutical Compositions

Administration of any of the present molecules can be achieved by any of the routes normally used for introducing a modulator compound into ultimate contact with the tissue to be treated. The modulators are administered in any suitable manner, optionally with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., Remington's Pharmaceutical Sciences, $17^{th}$ ed. 1985)).

The Chandra modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and nonaqueous solutions, isotonic sterile solutions, which can contain antioxidants, buffers, bacteriostats, and solutes that render the formulation isotonic, and aqueous and nonaqueous sterile suspensions that can include suspending agents, solubilizers, thickening agents, stabilizers, and preservatives. In the practice of this invention, compositions can be administered, for example, orally, nasally, topically, intravenously, intraperitoneally, intravesically or intrathecally. The formulations of compounds can be presented in unit-dose or multi-dose sealed containers, such as ampules and vials. Solutions and suspensions can be prepared from sterile powders, granules, and tablets of the kind previously described. The modulators can also be administered as part a of prepared food or drug.

The dose administered to a patient, in the context of the present invention should be sufficient to effect a beneficial response in the subject over time. The dose will be determined by the efficacy of the particular modulators employed and the condition of the subject, as well as the body weight or surface area of the area to be treated. The size of the dose also will be determined by the existence, nature, and extent of any adverse side-effects that accompany the administration of a particular compound or vector in a particular subject.

In determining the effective amount of the modulator to be administered in a physician may evaluate circulating plasma levels of the modulator, modulator toxicities, and the production of anti-modulator antibodies. In general, the dose equivalent of a modulator is from about 1 ng/kg to 10 mg/kg for a typical subject.

For administration, modulators of the present invention can be administered at a rate determined by the LD-50 of the modulator, and the side-effects of the compound at various concentrations, as applied to the mass and overall health of the subject. Administration can be accomplished via single or divided doses.

VIII. Transgenic Animals

Transgenic and chimeric non-human mammals and methods for generating them are described below. The mammals are useful, inter alia, for testing the function of Chandra in vivo, to generate models for the study of diseases and conditions associated with Th1 or Th2 cell activity, and for the development of potential treatments for diseases and conditions associated with Th1 cell activity (e.g. autoimmune disease or transplant rejection) or Th2 cell activity (e.g., allergy, asthma, and atopic diseases).

Transgenic and chimeric non-human mammals are generated that contain cells that lack at least one functional endogenous allele for chandra. A "chimeric animal" includes some cells that lack the functional chandra gene of interest and other cells that do not have the inactivated gene. A "transgenic animal," in contrast, is made up of cells that have all incorporated the specific modification which renders the chandra gene inactive or otherwise altered. While a transgenic animal is typically always capable of transmitting the mutant chandra gene to its progeny, the ability of a chimeric animal to transmit the mutation depends upon whether the inactivated gene is present in the animal's germ cells. The modifications that inactivate or otherwise alter the chandra gene can include, for example, insertions, deletions, or substitutions of one or more nucleotides. The modifications can interfere with transcription of the gene itself, with translation and/or stability of the resulting MRNA, or can cause the gene to encode an inactive or otherwise altered Chandra polypeptide, e.g., an Chandra polypeptide with modified binding properties or transport activity.

The methods of the present invention are useful for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., *Genetic Engineering of Animals*, VCH Publ., 1993; Murphy and Carter, Eds., *Transgenesis Techniques:Principles and Protocols* (*Methods in Molecular Biology*, Vol. 18), 1993; and Pinkert, C A, Ed., *Transgenic Animal Technology: A Laboratory Handbook*, Academic Press, 1994.

In preferred embodiments, transgenic mice will be produced as described in Thomas et al., (1999) *Immunol.* 163:978–84; Kanakaraj et al. (1998) *J. Exp. Med.* 187:2073–9; or Yeh et al., (1997) *Immunity* 7:715–725.

Typically, a modified chandra gene is introduced, e.g., by homologous recombination, into embryonic stem cells (ES), which are obtained from preimplantation embryos and cultured in vitro. See, e.g., Hooper, M L, *Embryonal Stem Cells: Introducing Planned Changes into the Animal Germline* (Modem Genetics, v. 1), Int'l. Pub. Distrib., Inc., 1993; Bradley et al. (1984) *Nature* 309, 255–258. Subsequently, the transformed ES cell is combined with a blastocyst from a non-human animal, e.g., a mouse. The ES cells colonize the embryo and in some embryos form the germ line of the resulting chimeric animal. See, Jaenisch (1988) *Science* 240: 1468–1474. Alternatively, ES cells or somatic cells that can reconstitute an organism ("somatic repopulating cells") can be used as a source of nuclei for transplantation into an enucleated fertilized oocyte giving rise to a transgenic mammal. See, e.g., Wilmut et al. (1997) *Nature* 385: 810–813.

Other methods for obtaining a transgenic or chimeric animal having a mutant chandra gene in its genome is to contact fertilized oocytes with a vector that includes a polynucleotide that encodes a modified, e.g., inactive, Chandra polypeptide. In some animals, such as mice, fertilization is typically performed in vivo and fertilized ova are surgically removed. In other animals, particularly bovines, it is preferably to remove ova from live or slaughterhouse animals and fertilize the ova in vitro. See DeBoer et al., WO 91/08216. In vitro fertilization permits the modifications to be introduced into substantially synchronous cells.

Fertilized oocytes are typically cultured in vitro until a pre-implantation embryo is obtained containing about 16–150 cells. The 16–32 cell stage of an embryo is described as a morula, whereas pre-implantation embryos containing more than 32 cells are termed blastocysts. These embryos show the development of a blastocoel cavity, typically at the 64 cell stage. The presence of a desired chandra mutation in the cells of the embryo can be detected by methods known to those of skill in the art, e.g., Southern blotting, PCR, DNA sequencing, or other standard methods. Methods for culturing fertilized oocytes to the pre-implantation stage are described, e.g., by Gordon et al. (1984) *Methods Enzymol.* 101: 414; Hogan et al. *Manipulation of the Mouse Embryo: A Laboratory Manual*, C.S.H.L. New York (1986) (mouse embryo); Hammer et al. (1985) *Nature* 315: 680 (rabbit and porcine embryos); Gandolfi et al. (1987) *J. Reprod. Fert.* 81: 23–28; Rexroad et al. (1988) *J. Anim. Sci.* 66: 947–953 (ovine embryos) and Eyestone et al. (1989) *J. Reprod. Fert.* 85: 715–720; Camous et al. (1984) *J. Reprod. Fert.* 72: 779–785; and Heyman et al. (1987) *Theriogenology* 27: 5968 (bovine embryos). Pre-implantation embryos may also be stored frozen for a period pending implantation.

Pre-implantation embryos are transferred to an appropriate female resulting in the birth of a transgenic or chimeric animal, depending upon the stage of development when the transgene is integrated. Chimeric mammals can be bred to form true germline transgenic animals. Chimeric mice and germline transgenic mice can also be ordered from commercial sources (e.g., Deltagen, San Carlos, Calif.).

Other methods for introducing mutations into mammalian cells or animals include recombinase systems, which can be employed to delete all or a portion of a locus of interest. Examples of recombinase systems include, the cre/lox system of bacteriophage P1 (see, e.g., Gu et al. (1994) *Science* 265: 103–106; Terry et al. (1997) *Transgenic Res.* 6: 349–356) and the FLP/FRT site specific integration system (see, e.g., Dymecki (1996) *Proc. Natl. Acad. Sci. USA* 93: 6191–6196). In these systems, sites recognized by the particular recombinase are typically introduced into the genome at a position flanking the portion of the gene that is to be deleted. Introduction of the recombinase into the cells then catalyzes recombination which deletes from the genome the polynucleotide sequence that is flanked by the recombination sites. If desired, one can obtain animals in which only certain cell types lack the chandra gene of interest, e.g., by using a tissue specific promoter to drive the expression of the recombinase. See, e.g., Tsien et al. (1996) *Cell* 87: 1317–26; Brocard et al. (1996) *Proc. Natl. Acad. Sci. USA* 93: 10887–10890; Wang et al. (1996) *Proc. Natl. Acad. Sci. USA* 93: 3932–6; Meyers et al. (1998) *Nat. Genet.* 18:136–41).

The presence of any mutation in a chandra gene in a cell or animal can be detected using any method described herein, e.g., Southern blot, PCR, or DNA sequencing. See, e.g., Ausubel et al., supra.

IX. Kits chandra genes and their homologs are useful tools for identifying Th1 cells, for forensics and paternity determinations, and for examining the number of Th1 cells or the degree of Th1 polarization in a cell or cells. Chandra specific reagents that specifically hybridize to chandra nucleic acids, such as chandra probes and primers, and Chandra specific reagents that specifically bind to or modulate the activity of a Chandra protein, e.g., Chandra antibodies or other compounds are used to examine Th1 cell polarization and regulation as well as to treat Th1 or Th2 associated diseases or conditions.

Nucleic acid assays for the presence of DNA and RNA for a chandra polynucleotide in a sample include numerous techniques known to those skilled in the art, such as Southern analysis, Northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al., eds. 1987). In addition, a Chandra protein can be detected with the various immunoassay techniques described above. The test sample is typically compared to both a positive control (e.g., a sample expressing a recombinant Chandra protein) and a negative control.

The present invention also provides for kits for screening for modulators of Chandra proteins or nucleic acids. Such kits can be prepared from readily available materials and reagents. For example, such kits can comprise any one or more of the following materials: Chandra nucleic acids or proteins, reaction tubes, and instructions for testing Chandra activity. Optionally, the kit contains a biologically active Chandra protein. A wide variety of kits and components can be prepared according to the present invention, depending upon the intended user of the kit and the particular needs of the user.

EXAMPLES

Cloning of Chandra cDNA Based on Subtractive Hybridization

A PCR-based cDNA subtraction method (Diatchenko et al. (1996) *PNAS* 93: 6025–6030) was used to identify novel genes that are upregulated during in vitro differentiation of naive T cells into Th1 cells. In order to promote Th1 or Th2 differentiation, total splenocytes were stimulated for 7 days with plate-bound anti-CD3 (2C11, 2 μg/ml), in the presence of IL-12 (5 ng/ml, R&D Systems, Minneapolis, Minn.) and anti-IL-4 (11B11, 5 μg/ml, PharMingen, San Diego, Calif.) for Th1 differentiation, and IL-4 (10 ng/ml, Biosource International, Inc., Camarillo, Calif.) and anti-IL-12 (1 μg/ml, R&D Systems) for Th2 differentiation. The cultures were supplemented on days 2 and 4 with recombinant murine IL-2 (10 ng/ml, R&D Systems). All cells were harvested on day 7 and used for further analysis. In some experiments, enriched CD4$^+$ cells were prepared by negative selection using CD4$^+$ T cell enrichment columns. The purity of the cells were routinely verified by flow cytometry, and ranged between 75–85%. In experiments involving purified T cells, mitomycin C-treated splenocytes were added in addition to the stimulants described above.

After 7 days of stimulation, Th1 and Th2 cells were harvested and poly-A$^+$ MnRNA was prepared using the FastTrack 2.0 kit (Invitrogen Corporation, Carlsbad, Calif.). Subtractive hybridization was performed using a commercial differential PCR-Select Kit (Clontech, Palo Alto, Calif.). Briefly, total cDNA was synthesized from 2 μg of either Th1 or Th2 MRNA. The cDNAs were digested with RsaI, and ligated independently to two different adaptors. After two rounds of hybridization (Th1 cDNAs with excess of Th2 cDNAs), and PCR amplification, the PCR products were ligated into a T/A cloning vector (Invitogen). Approximately 136 independent colonies were analyzed by colony hybridization, and 26 cDNAs were found to be differentially expressed in the Th1 pools. The differential expression of various cDNAs was verified by Northern analysis using total RNA prepared from Th1 and Th2 cells.

Several novel genes, as well as previously described genes, such as, IFN-γ and granzyme B, that were differentially upregulated during Th1 differentiation were identified. One novel gene, designated chandra (means "moon" in the Sanskrit language), had no significant sequence similarity to previously described genes, and was selected for further characterization. The amino acid sequence of Chandra is shown as FIG. 1.

To confirm the differential expression of chandra mRNA in the helper T subsets, enriched CD4$^+$ cells were activated in vitro under Th1 or Th1 differentiation conditions. Total RNA was prepared using Trizol reagent (Life Technologies, Gaithersburg, Md.), and approximately 10–20 μg of total RNA was subjected to Northern blot analysis using the ExpressHyb hybridization solution (Clontech). The internal primers used to generate the chandra probe were as follows: sense, 5' CCCACTTCAGTGATGTTAATGGTC (SEQ ID NO:3) and anti-sense, 5' CAAATCCTGTTGAGACAGT-GATGGC (SEQ ID NO:4). In all the experiments, the same blots were stripped and reprobed for either IL-18R or β actin. Under these conditions, expression of chandra was observed only in Th1 cells. Activation of T cells with anti-CD3 plus IL-2 alone did not induce chandra mRNA. As expected, differential upregulation of IL-18R expression was also observed in Th1 cells. Expression of chandra was also observed in a Th1 (AE7) but not Th2 (D10.G4) clone. These observations established chandra as a Th1-specific gene.

In order to determine whether chandra was exclusively expressed in Th1 subsets, the expression pattern of chandra in various tissues was examined using Northern blot analysis. chandra transcripts were found in liver, brain, heart, lung, spleen, testis and ovary, and were in low abundance in the thymus, kidney and embryo (10–12d). Different splice variants of chandra mRNA were observed in the testis. Furthermore, higher constitutive expression of chandra mRNA was seen in spleen compared to thymus.

Chandra is a Four-transmembrane Domain Protein Expressed on the Cell Surface

The open reading frame of chandra encodes a novel protein of 226 amino acid residues with four potential membrane-spanning regions (FIG. 1) with no significant homology to any known genes. To determine if Chandra is present on the cell surface, a mammalian expression vector encoding Chandra fused to a C-terminal Flag epitope tag was constructed. 293HEK cells were transfected with either control vector or a carboxy-terminal Flag epitope tag construct of Chandra, using the calcium phosphate method (Promega). Forty-eight hours post-transfection, cells were stained with anti-Flag antibody (Sigma, St. Louis, Mo.), followed by PE-conjugated anti-mouse secondary antibody (Caltag Laboratories, Burlingame, Calif.). PE positive cells were detected by flow cytometry and analyzed using the CellQuest program (Becton Dickinson, San Jose, Calif.).

Cell surface expression of Chandra was detected in 293HEK cells. These experiments indicated that Chandra is a cell surface protein and the C-terminus of the protein was exposed on the surface.

Chandra Expression in Th1 Lymphocytes is Regulated by a STAT4- or STAT1-independent Signaling Pathway Several studies have shown that IL-12-dependent STAT4 activation is important for the generation of Th1 cells (Kaplan et al. (1996) *Nature* 382.174–177; Thierfelder et al. (1996) *Nature* 382: 171–174). Therefore, the requirement of STAT4 signaling events for chandra expression in Th1 cells was determined. CD4$^+$ T cells from STAT4 deficient mice were differentiated in vitro under Th1 or Th2 conditions, and chandra expression was determined using Northern blot analysis. Similar to wild type CD4$^+$ T cells, chandra mRNA was observed only in STAT4-deficient Th1 cells, and was barely detectable in undifferentiated cells or in Th2 cells.

T cell receptor crosslinking has been shown to result in IFN-γ production by Th1 cells (Carter and Murphy (1998) *J. Exp. Med.* 189: 1355–1360). In order to test whether chandra is an IFN γ-responsive gene, total splenocytes from IFN-γ deficient mice (Jackson laboratories, Bar Harbor, N.Y.) were activated with anti-CD3 and IL-12 plus anti-IL-4, or IL-4 plus anti-IL-12. Low amounts of chandra transcripts were expressed in unstimulated splenocytes. Following activation of splenocytes with anti-CD3 and IL-12 plus anti-IL-4, a significant increase in chandra mRNA was observed. Consistent with the earlier experiments, co-stimulation of splenocytes with anti-CD3, IL-4, and neutralizing anti-IL-12 antibodies, greatly reduced the expression of chandra. Similar observations were obtained when CD4$^+$ T cells from STAT1-deficient mice were differentiated under Th1 or Th2 conditions. Taken together, these data clearly showed that chandra is not an IFN-γ responsive gene, and its expression in Th1 lymphocytes was independent of signaling via the two transcription factors, STAT4 or STAT1.

Expression of Chandra is Repressed by IL-4 Via a STAT6-dependent Signaling Pathway STAT6 activation plays a crucial role in the development of Th2 cells. Since chandra mRNA is not detected in Th2 cells, the influence of IL-4-induced signal transduction on chandra expression was determined. STAT6-deficient CD4$^+$ cells were activated under neutral, Th1 or Th2 differentiation conditions, and chandra expression was examined by under different stimulation conditions. Similar to wild type and STAT4 deficient mice, chandra mRNA was readily detectable in STAT6-deficient Th1 cells. chandra expression was also observed when T cells were differentiated under Th2 conditions. This was expected since STAT6 deficient mice are severely defective in generating Th2 cells (Kaplan et al. (1996) *Immunity* 4: 313–319). Surprisingly, chandra transcripts could also be detected in anti-CD3 activated T cells. These results provide evidence that expression of chandra in undifferentiated T cells and Th2 cells could be negatively regulated via STAT6-dependent signaling events.

To directly test if IL-4 signaling repressed chandra expression, T cells from wild-type mice were incubated with anti-CD3 in the presence of excess amounts of neutralizing anti-IL-4 antibodies. Addition of anti-IL-4 but not control IgG was sufficient to induce chandra transcripts in anti-CD3 activated T cells. Collectively, these results clearly demonstrate that expression of chandra in T cells is facilitated during IL-4 neutralization conditions, which is usually seen during differentiation of helper T cells in to Th1 effector populations.

Chandra Inhibits IL-4 Induced Gene Transcription

Results from previous experiments indicated that the expression of chandra in Th2 cells was suppressed by STAT6 dependent signaling events. Since IL-4 dependent STAT6 activation was critical for the development of Th2 effectors, the ability of Chandra to influence IL-4 induced transcription was investigated. To study IL-4 induced gene expression, we used an IL-4 response element derived from the human inununoglobulin eavy chain germline ε promoter containing a prototypical N4 STAT6 binding site lanked by a C/EBP binding site (Mikita et al. (1996) *Mol Cell. Biol.* 16: 5811–5820). Jurkat cells were co-transfected with the IL-4 inducible reporter construct, and various amounts of chandra expression plasmid. As shown in FIG. 2, co-transfection of chandra significantly inhibited IL-4 induced luciferase activity in a dose-dependent manner. In contrast, chandra expression did not affect luciferase activity driven by an IFN-γ inducible reporter or a constitutively active reporter construct.

To test the possibility that four transmembrane proteins, in general, inhibited IL-4 signaling, the effects of CD81, a cell surface protein usually found in lymphoid and myeloid cells, on IL-4-induced gene transcription was examined. co-transfection of CD81 in Jurkat cells did not affect IL-4 induced luciferase activity Several of the four-transmembrane proteins described so far are found in molecular complexes with other cell surface proteins. Thus, it is possible that overexpression of Chandra could result in its association with the IL-4 receptor (IL-4R) complex, consequently disrupting IL-4-dependent signaling events. Thus, it was determined whether overexpression of additional IL-4Rα chains could counteract the inhibitory effect of Chandra on IL-4 induced gene transcription. Jurkat cells were co-transfected with an IL-4R α expression plasmid using the Superfect reagent (Qiagen GmbH, Hilden, Germany), and different amounts of the chandra expression construct, and luciferase activity was measured after IL-4 stimulation. A control plasmid carrying the β-galactosidase gene under the control of CMV promoter was co-transfected in each experiment. After 24 h of transfection, cells were stimulated for an additional 20 h with 10 ng/ml of appropriate cytokines. Luciferase and β-galactosidase assays were performed using the Promega assay system (Promega, Madison, Wis.).

The inhibitory effects of Chandra on IL-4-induced gene transcription was completely overcome by overexpression of the IL-4R α chain. Collectively, these results indicate that Chandra inhibited IL-4 dependent signaling pathway in T cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. An isolated nucleic acid encoding a polypeptide expressed in Th1 lymphocytes, said polypeptide comprising at least about 95% amino acid sequence identity to SEQ ID NO:1 over the full length of the sequence, and said polypeptide possessing the ability to inhibit IL-4 dependent signaling.

2. The nucleic acid of claim 1, wherein said nucleic acid encodes a polypeptide that specifically binds to polyclonal antibodies generated against a polypeptide having the amino acid sequence of SEQ ID NO:1.

3. The nucleic acid of claim 1, wherein said nucleic acid encodes a polypeptide comprising the amino acid sequence of SEQ ID NO:1.

4. The nucleic acid of claim 1, wherein said nucleic acid hybridizes in a buffer of 40% formamide, 1 M NaCl, 1% SDS at 37° C., and a wash in 1×SSC at 45° C., performed for 5, 15, 30, 60, 120, or more minutes, to the complement of a nucleic acid comprising the nucleotide sequence of SEQ ID NO:2.

5. The nucleic acid of claim 1, wherein said nucleic acid hybridizes in a buffer of 50% formamide, 5×SSC, 1% SDS at 42° C., or, 5×SSC, 1% SDS at 65° C., and a wash in 0.2×SSC, and 0.1% SDS at 65° C., performed for 5, 15, 30, 60, 120, or more minutes, to the complement of a nucleic acid comprising the nucleotide sequence of SEQ ID NO:2.

6. The nucleic acid of claim 1, wherein said nucleic acid comprises the nucleotide sequence of SEQ ID NO:2.

7. An expression cassette comprising the nucleic acid of claim 1.

8. An isolated cell comprising the expression cassette of claim 7.

9. The nucleic acid of claim 1, wherein said nucleic acid encodes a polypeptide that promotes Th1 cell differentiation and production.

10. The nucleic acid of claim 1, wherein said nucleic acid encodes a polypeptide that inhibits Th2 cell differentiation and production.

11. The nucleic acid of claim 1, wherein said nucleic acid encodes a polypeptide that inhibits IL-4 activity in Th2 cells.

12. The nucleic acid of claim 1, wherein said nucleic acid encodes a polypeptide comprising an N-terminal domain, four transmembrane domains, an extracellular loop, two cytoplamic loops and a C-terminal domain.

13. An expression cassette comprising the nucleic acid of claim 2.

14. An isolated cell comprising the expression cassette of claim 13.

15. An expression cassette comprising the nucleic acid of claim 3.

16. An isolated cell comprising the expression cassette of claim 15.

* * * * *